(12) United States Patent
Liu et al.

(10) Patent No.: US 10,178,948 B2
(45) Date of Patent: Jan. 15, 2019

(54) SELF OPERATABLE OPHTHALMIC DEVICE

(71) Applicant: Miraco Light Inc., San Jose, CA (US)

(72) Inventors: Qingdi Liu, San Jose, CA (US); Ming Cai, Milpitas, CA (US)

( * ) Notice: Subject to any disclaimer, the term of this patent is extended or adjusted under 35 U.S.C. 154(b) by 0 days.

(21) Appl. No.: 15/591,966

(22) Filed: May 10, 2017

(65) Prior Publication Data
US 2017/0325675 A1   Nov. 16, 2017

Related U.S. Application Data

(60) Provisional application No. 62/334,913, filed on May 11, 2016.

(51) Int. Cl.
| | |
|---|---|
| *A61B 3/00* | (2006.01) |
| *A61B 3/024* | (2006.01) |
| *A61B 3/113* | (2006.01) |
| *A61B 3/12* | (2006.01) |
| *A61B 3/18* | (2006.01) |

(52) U.S. Cl.
CPC .......... *A61B 3/0041* (2013.01); *A61B 3/0025* (2013.01); *A61B 3/0033* (2013.01); *A61B 3/024* (2013.01); *A61B 3/113* (2013.01); *A61B 3/12* (2013.01); *A61B 3/18* (2013.01)

(58) Field of Classification Search
CPC ........... A61B 3/14; A61B 3/0025; A61B 3/12; A61B 3/102; A61B 3/0058
USPC .......................................................... 351/206
See application file for complete search history.

(56) References Cited

U.S. PATENT DOCUMENTS

| | | | | | |
|---|---|---|---|---|---|
| 9,201,512 | B1 * | 12/2015 | Raffle | ..................... | G06F 3/033 |
| 9,625,723 | B2 * | 4/2017 | Lou | ..................... | G02B 27/0172 |
| 9,684,827 | B2 * | 6/2017 | Zhang | ................ | G06K 9/00604 |
| 2017/0205876 | A1 * | 7/2017 | Vidal | ..................... | G01S 17/88 |

* cited by examiner

*Primary Examiner* — Mohammed Hasan
(74) *Attorney, Agent, or Firm* — Intellectual Property Law Group LLP (57) ABSTRACT

The invention provides a system for a patient to obtain quality eye tests results without other people's assistance. The system includes a wearable, head-mounted, ophthalmic device. With a head mounted structure, the patient's head position remains still relative to the ophthalmic device. One or more "iris" cameras and a display screen are used to help align the patient's eye on ocular lenses for optimal eye test results. The system includes a patient interface module that allows the patient to operate the device. Accessory features such as a microphone and earphones are used to communicate with a close by stander during and after the eye exam. Another key feature is a cloud service connection used to store test results for remote access by the patient or other authorized persons.

19 Claims, 8 Drawing Sheets

SELF OPERATABLE OPHTHALMIC DEVICE

This application claims priority to the U.S. provisional patent application Ser. No. 62/334,913, filed on May 11, 2016, the contents of which are incorporated by reference herein.

FIELD OF THE INVENTION

The present invention generally relates to optical instruments and devices used for detecting dysfunctions in human's vision and/or imaging the retina/cornea of the human eye. More particularly, the invention relates to a wearable, head mounted, ophthalmic device platform that enables the patient to align him or herself to the optical system of the device, and obtain quality test results without any medical personnel or another person's assistance.

BACKGROUND OF THE INVENTION

Ophthalmic devices such as a visual field analyzer, fundus camera, scanning laser ophthalmoscopy, optical coherence tomography (OCT) imager, and other instruments, have been traditionally operated in a clinical setting and by qualified medical professional. Eye alignment has remained a challenging problem for these devices. In order to keep the patient's head in a fixed position and distance from the device, there typically involves a structure frame with a head rest and a chin rest, on which the patient can rest the forehead and the chin.

When a visual field analyzer is used, the patient is presented with a series of light stimuli of varying intensities in different visual field locations, and the sensitivity of the retina is assessed based on the patient's ability to consciously detect and respond to these stimuli. The visual field test requires one of the patient's eyes be covered with a patch and the gaze be fixed on a spot in the center of the visual field. In order to obtain a successful map of the visual field, the patient must be able to maintain a fixed head position in relation to the test instrument and a constant gaze toward the fixation. However, even with today's computer assisted perimeter, it normally takes 5 to 10 minutes to complete the test on one eye. The influence of a patient's fatigue on the test results cannot be underestimated and remains a major challenge for test reliability and accuracy. It also happens that the patient's eye moves suddenly, such as blinking, saccades, etc., at the moment the stimulus is presented, and thus directly affects the test results.

In another option, a fundus camera is used. The fundus of the eye is the interior surface of the eyeball, including the retina which functions as a light-sensitive screen, the optic disc which is the head of the nerve to the eye, and the macula which is the small spot in the retina where vision is keenest. The device used to capture a photograph of the fundus, often expensive and sophisticated, is called Fundus Camera. To obtain high quality fundus photography can be very challenging. Any misalignment of the patient's eyeball to the imaging optics may lead to unacceptable results. Furthermore, the patient's unconscious head and eye movement can also happen at the moment when the medical staff presses the capture button, resulting in an unsuccessful attempt. However, none of the fundus cameras in the market today can effectively alleviate the problem because the device operator could not anticipate the patient's possible reaction. As a matter of fact, the quality of the fundus photography highly relies on the experience and skills of the device operator, which has hindered the device's usage, particularly in areas where the trained medical professionals are not easily accessible.

In another instance, a scanning laser ophthalmoscopy (SLO) is used. The SLO is an imaging technology that scans a focused laser beam point by point or line by line on the retina and then captures the reflected light to construct an image of the retina. Due to the scanning mechanism, it usually takes a few seconds to obtain a complete SLO image, and thus the patient's head and eye stability is even more critical in order to obtain an SLO image of good quality. In fact, some instruments have to employ a technique so-called retina tracking to dynamically adjust the scanning spot following any head and/or eye movement at a cost of system complexity and expense.

In another instance, an optical coherence tomography (OCT) imager is used. Similar to the SLO, the OCT also scans a focused laser beam point by point on the retina/cornea, and then the scattered light from the retina/cornea tissue is combined with the light from a reference arm in a low-coherence interferometer, and a cross-section image of the retina/cornea is reconstructed based on the interference patterns. Due to the scanning mechanism, OCT also requires a few seconds to complete the scan and consequently faces the same challenges as the SLO in regards to the patient head/eye movement.

Traditionally, the ophthalmic devices described above, are designed to be used by a trained operator. The patient is expected to follow the instruction from the operator passively, except pressing the response button during a perimetry test. Even after being requested to stabilize his/her head and fixate his/her eye gaze throughout the test, the patient's eyes could move involuntarily at any moment, and the head could drift away from the device with a grasp of breath. All these factors make the traditional ophthalmic exams non-trivial even with a trained operator.

What is desired is a wearable, head mounted, ophthalmic device platform that enables the patient to align him or herself to the optical system of the device, and obtain quality test results without any medical personnel or another person's assistance.

SUMMARY OF THE INVENTION

The present invention describes a wearable, head mounted, ophthalmic device platform that enables the patient to align him or herself to the optical system of the device, and obtain quality test results without any medical staff or another person's assistance. As in sharp contrast to the traditional methods where the patients are only the passive subject of the exam, the present invention not only lets the patient participate in the whole process, but also allows the patient fully control the pace of the test.

The ophthalmic device according to the invention includes components such as a head mounted structure, like a goggle or a helmet, so that the patient's head position remains still relative to the ophthalmic device. Also, an "iris" camera system that records images or video streaming of the patient's iris/pupil during the exam. The patient's eyeball position and/or gaze direction are then analyzed based on the information obtained on the camera system. Two iris cameras, one for each eye can also be used. A display screen, such as the LCD or OLED displays used on cell phones, is included, to display fixation target and/or other information necessary to guide the patient to optimize the alignment, and complete the eye test. The display screen can be implemented as two discrete displays, one for each eye, or as one larger display with the screen split for each eye. In addition, a patient interface (PI) module for the patient to interact with the device is further implemented. The PI module can be integrated into the head mount structure, but preferably, it is a push button device operably connected to the device wirelessly, such as Bluetooth or with a cable, such as a USB connection. The PI module can have one or more buttons as necessary for the application. The PI module can also be an assembly of one or more sensors that collect the patient's various responses. The patient interface can also be through audio devices, such as a microphone and an earphone. Additional accessories can be added to the ophthalmic device, such as a modem for Internet connection to support communications with another person remotely. Furthermore, a cloud service connection can be implemented to store test results for remote access by the patient or other authorized persons. Biometric identification to enhance security and privacy of the patient data can also be achieved with the iris scans (using the device iris cameras) or fingerprints. And finally, an app, run on a second computer, tablet or smart phone, allows the medical professional to view the display screen on the ophthalmic device remotely, assign the test protocol, monitor the test progress, interact with the patient under test and review test results.

The present invention creates a much more comfortable test environment. The patient is completely immersed in the test device with only views to the test screen while no ambient light influences the test results. There is no need to block one eye when the other eye is under test. Both eyes are presented with a fixation target on the center of their own screen, which helps keep both eyes relaxed while fixing the gaze. Furthermore, no medical professional is needed to assist the patient to perform the exam. This is a significant advantage as it allows the exams to be taken at virtually anywhere besides the hospitals or clinics. Once the patient puts on the head mounted ophthalmic device comfortably, the device first aligns to the patient's eyes automatically. The patient can then decide to start whenever he or she is ready by pressing a button. Because the control is all on the patient, it is more likely that the patient has the best attention as the test starts and the retina image can be captured with no or much less unconscious blinks or saccades. Finally, the head mount or goggle-like structure allows the device to be held still related to the patient's head position during the test and creates a comfortable and immersive environment for the patient to focus on the exam and operate the device by him or herself. In fact, the patient can relax his or her head and take the exam while sitting, standing or laying down. The exam can also be paused temporarily and resumed at a later time.

First Preferred Embodiment

In one embodiment of the present invention, a visual field analyzer is provided. While worn on the head, the patient's left and right eyes have a field of view covered by the left and right screen areas, respectively. For a practical application, the ocular lens, placed between the patient's eye and the display screen, is designed so that the view angle for each eye is at least 60 degrees, i.e. at least 30 degree from the center. Then an infrared camera focused at the patient's iris/pupil, one for each eye, is placed in the system using a visible/infrared beam splitter/combiner. Off-axis infrared illumination, which is invisible to the patient, for the patient's iris/pupil can be conveniently placed close to the patient's eyes.

A control unit that presents test stimuli on the screen following the visual field testing strategy is displayed and a push button or a touch sensor for the patient is available to respond. This device offers many advantages over the traditional visual field analyzer. There is no need to switch eyes or to patch one eye while the other one is under test because each eye sees its own screen. The test stimuli can be presented on the two independent screens sequentially, or alternatively only one stimulus at a time, so that the two eyes can be tested in a single continuous procedure. In addition, the head-mounted design ensures the patient's eye is aligned to the device optical axis and remains unchanged during the test, which is critical for accurate testing and reliable results. It also allows the test to be paused and resumed at any time. Because the same patient alignment can be achieved and maintained for every repeated test, visual field progressive changes can be reliably assessed based on two or more repeated tests taken over a period of time.

Second Preferred Embodiment

In yet another preferred embodiment of the present invention, the invented ophthalmic device platform can be used to build a self-operable fundus camera. Fundus illumination optics can be added to the system and the iris cameras can be used to take the fundus photography with appropriate arrangement of focusing optics. Dedicated fundus cameras can also be designed and the iris cameras can be moved to the off-axis locations so that the patient's eyes can be continuously monitored with the iris cameras. The display screen is used to present the fixation targets for both eyes and the easy-to-follow instructions for the patient to guide through the eye alignment and image capturing steps.

When the same cameras are used for both the iris and the fundus, the camera is first focused on the patient's pupil and iris to assist with the eye alignment. Once a good eye alignment is achieved, the camera is then adjusted to focus on the patient's retina. In conjunction with the camera focus adjustment, the position of the display screen relative to the patient's eye can be tuned simultaneously so that as soon as the fixation target on the display screen appears to be in focus to the patient, the camera's focus is also right on the patient's retina. The patient can thus follow this cue to place the camera focus on their retina. The cameras in this case should work for both infrared and visible wavelengths. To obtain a white or any other visible light illuminated fundus photography, the IR illumination light should be turn off at the time of capturing.

When separated cameras are used, the patient's eyes are constantly monitored by the iris cameras during the fundus image capturing. The conjunctive adjustment of the fundus camera focus and the display screen with fixation targets can be also implemented to guild the patient with the alignment. In this case, the iris cameras can be designed to work for IR band only, while the fundus camera for visible band only. There is no need to turn off IR illumination when the fundus image is being captured.

Instead of capturing one still image of the fundus, the camera can also consecutively capture a series of still images or record a video stream while the camera focus is swept over a range of distance. The fundus image with the best focus and thus best quality can be located by analyzing the set of still images or the frames in the video stream. This is similar to the auto-focus function as built-in with many cameras, and more objective as compared to the previously mentioned method where the patient has to place the camera's focus on his/her retina based on his/her judgment on the fixation target sharpness.

Once the eye to device alignment is achieved, the patient can then take time to prepare him or herself by opening eyes wide and looking at the fixation target before pressing the image capture button. Since the patient is the lead of the process, it is much less likely blinks or saccades happen during the capture. Even if the captured fundus image is not optimal, the patient can immediately repeat the capture because the eye to device alignment remains unchanged. In fact, the fixation target can move to different locations to guide the patient's eye so that a collection of the patient's fundus images covering a large retina area can be taken one by one.

Third Preferred Embodiment

In yet another preferred embodiment of the present invention, the invented ophthalmic device platform can be used to build a self-operable scanning laser ophthalmoscopy (SLO) or optical coherence tomography (OCT) imaging devices. A high-speed laser scanner is used. Coupled with a series of optics lenses (scan lens, ocular lens, etc.), the laser beam is focused and projected onto the area of interest on the patient's eye, such as the posterior segment (retina) and the anterior segment (cornea), etc. When the anterior segment is to be imaged, the SLO and OCT imaging optics is pre-aligned with the iris camera such that the SLO and OCT laser beam is focused on the cornea as soon as the iris camera comes to focus on the pupil and iris. When the posterior segment is to be imaged, the patient alignment procedure is similar to that for the fundus camera. The SLO and OCT imaging optics can move in conjunction with the display screen (fixation target) and/or the iris camera optics. Once the eye to device alignment is achieved with the help of the iris camera, the fixation targets or the iris camera are used to locate the patient's retina and subsequently to align the SLO and OCT imaging optics to the retina. The SLO and OCT images can also be used alone or assist with locating the retina by analyzing the image strength and contrast.

Once the patient alignment is achieved, the SLO and OCT images can be acquired repeatedly without concerns on the patient to device alignment changes as associated with traditional devices. In fact, it usually takes a few seconds to acquire one SLO and OCT image, and it is likely that the patient may blink and/or have saccades during the acquisition. The present inventions, however, allows almost unlimited time window for the patient to acquire an image with good quality. The device can continue acquiring images until acceptable images are captured. The iris camera, on the other hand, can further assist the image acquisition by detecting when the blinks or saccades actually happen. The frames or pixels acquired during that period are thus marked as bad and will be re-acquired. A fast iris and pupil detection algorithm can also be implemented to track the patient's gaze and the gaze direction is fed back to the optical scan controller in real time. If the patient's gaze is shifted away from the fixation target, the optical scanner applies with appropriate offsets accordingly to make sure the laser beam is projected to the correct locations on the retina for the data acquisition. With recorded gaze data, post-acquisition analysis can also be implemented to reveal the physical locations of the laser beam on the patient's retina, which is then used to register each frame or pixel in the image. This is very useful to remove motion artifacts that are very common in SLO and OCT images.

DETAILED DESCRIPTION OF THE INVENTION

While the present invention may be embodied in many different forms, designs or configurations, for the purpose of promoting an understanding of the principles of the invention, reference will be made to the embodiments illustrated in the drawings and specific language will be used to describe the same. It will nevertheless be understood that no limitation or restriction of the scope of the invention is thereby intended. Any alterations and further implementations of the principles of the invention as described herein are contemplated as would normally occur to one skilled in the art to which the invention relates.

Figure 1:
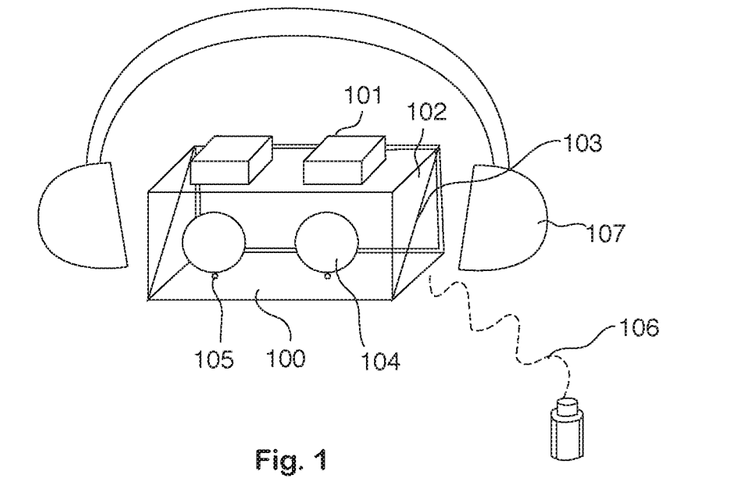
FIG. 1 is a perspective view illustration of the ophthalmic device platform according to the present invention.

FIG. 1 is a perspective view illustration of the ophthalmic device platform according to the present invention. In this illustration, several key features inside the wearable ophthalmic device are shown including the head-mounted structure, on-axis cameras, ocular lenses, beam splitter, infrared illumination light emitting diodes (LEDs), display screen and patient interface module, etc. When a patient uses the wearable device, his or her eyes are aligned through the ocular lenses. A patient interface module is operably connected to the wearable device wirelessly or with a cable for the patient to operate the device by him or herself. The patient interface module can be an assembly of one or more sensors that collect the patient's various responses. The head mounted structure 107, which can be in a shape of a goggle or a helmet, is for the patient to wear on during an eye test. His or her head position remains still relative to the ophthalmic device. The components illustrated in FIG. 1 can be held still relative to the patient's head position. Inside of the head mounted structure 107 an ophthalmic device 100 shown in FIG. 1 contains a pair of on-axis cameras 101. The patient wears the head mounted structure and the patient's eyes are centered in the ocular lenses 104. Just under the ocular lenses 104, is the infrared illumination light emitting diode (LED) 105. Behind the ocular lenses 104, a visible or infrared beam splitter 103 is used. Behind the beam splitter 103 is the high definition display screen 102. The patient interface module 106 is communicatively connected to the device through a cable or wirelessly.

Figure 2:
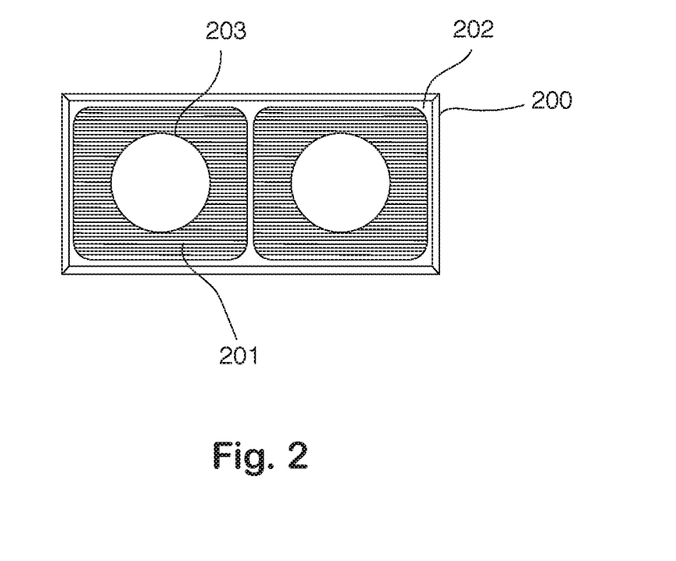
FIG. 2 is a front view illustration of the ophthalmic device platform showing two designated screen areas for each eye.

FIG. 2 is a front view of then ophthalmic device platform 100 described in FIG. 1 as if the patient is viewing the display screen 202 through his or her eyes. This is an improved and key feature of the wearable ophthalmic device. By having split display screen functionality, a dedicated screen area for each eye will help fixate and relax the non-tested eye and improve test reliability. Once the patient wears the head mounted device, there is a dedicated screen 201 for each eye. Fixation target, operation instructions, test stimuli or test results can be displayed on the screen 201. When one of the patient's eyes undergoes a test through the Ocular lenses 203, the other eye need not be closed or blocked with an eye patch. The screen dedicated to the non-tested eye can be completely dark or, even better, presents a fixation target to help stabilize this non-testing eye and minimize the influence on the tested eye. With the design described in FIG. 2, a comfortable test environment is created. The patient is completely immersed in the test device with only views to the test screen. There is no influence of ambient light on the test results, involuntary head movement related to the device is eliminated, and both eyes are relaxed but fixated to the target. Therefore, the eye exams can be executed with efficiency, quality and reliability.

Figure 3:
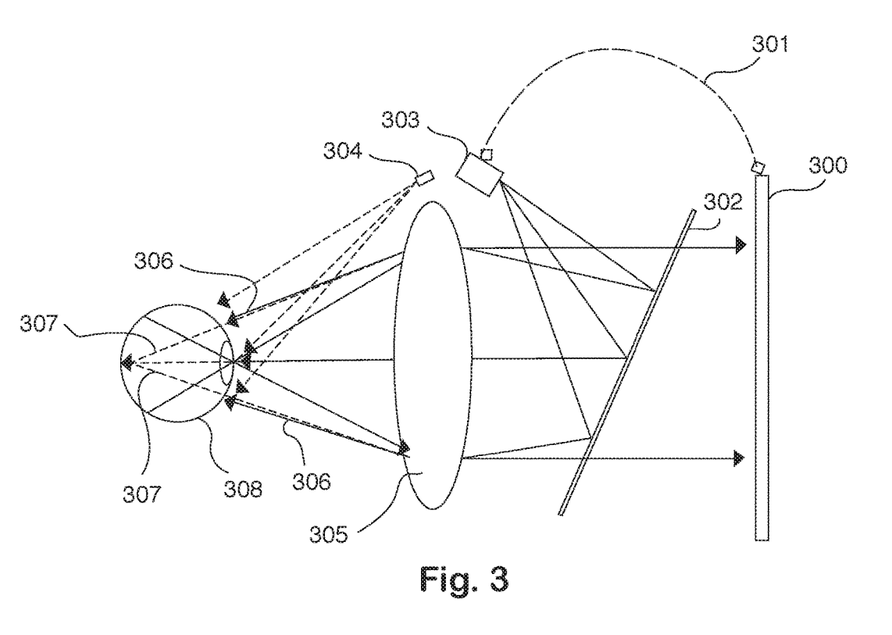
FIG. 3 is a side view illustration of the ophthalmic device platform according to FIG. 1.

FIG. 3 is a side view of then ophthalmic device platform 100 described in FIG. 1. In this illustration, again, several key features inside the wearable ophthalmic device are shown including the on-axis cameras, ocular lenses, beam splitter, infrared LED, and display screen. When the patient uses the wearable device, his or her eyes are aligned through the ocular lenses. Off-axis cameras and coupled focusing adjustment mechanism are also introduced as options to the device. All key components for an ophthalmic device in FIG. 1 are shown in FIG. 3 for the purpose of clarity and simplicity. Patient's eyes 308 are aligned and centered in the ocular lenses 305 and focuses on the display screen 300. A pair of on-axis cameras 303 (only one is shown), combined with the optical beam splitter 302, can be used to capture the iris image of the patient, as illustrated with the solid ray traces 306. The on-axis cameras 303 can also be designed to focus on the patient's retina, as illustrated with the dotted ray traces 307. With appropriate optical design, the on-axis cameras 303 can be switched to operate in iris mode or in retina mode as needed. While the on-axis cameras 303 operate in retina mode, the focus adjustment mechanism can be coupled with that of the display screen 300 as illustrated by the dotted line 301, so that as soon as the on-axis cameras 303 are focused on the patient's retina, the display screen 300 is also on focus to the patient's eyes, and vice versa. If continuous iris monitoring is needed for the application, an additional pair of off-axis iris cameras 304 are used, and can be placed just next to the ocular lenses 305. The on-axis camera 303 can then be configured to operate in constant retina mode. If there is no need for a retina mode operated cameras in some applications, for simplicity, only one set of on-axis cameras 303 or off-axis cameras 304 are used. The beam splitter 302 can also be removed if the on-axis cameras 303 are removed.

Key functionalities supported by the platform and components described in FIG. 1, FIG. 2 and FIG. 3 allow a patient to align him or herself to the optical system of the device, operate the device using the patient interface module and obtain quality test results without any medical staff or another person's assistance.

Patient's eye position, gaze direction and the device working distance (i.e., the distance between the ocular lens and the eye) are all detected with the on-axis iris cameras 101 described in FIG. 1 or the off-axis iris cameras 304 described in FIG. 3. Combined with the head-mounted structure 107, a very stable and precise eye to device alignment can be automated and maintained throughout the exam. The distance between the two ocular lenses 104 can be adjusted to fit the patient's pupil distance. The eye to ocular lenses 104 distance can be set based on the iris image contrast (clear and sharp). Patient's gaze direction can be reliably monitored in real time with an initial gaze calibration step (giving sufficient computation power of the control unit).

The patient's eye refractive error need to be corrected for many ophthalmic exams. For example, the patient eye should be able to focus on the display screen of a visual field analyzer where test stimuli are presented; the illumination light and the camera sensor of a fundus camera should be focused on the patient's retina surface to take a retina photograph; the laser beam and the detection optics in an SLO and OCT imaging system should also be focused on the patient's retina to capture a retina image.

With the device described in FIG. 1, refractive error correction can be performed manually with the patient's cooperation and judgment if appropriate visual guidance is presented on the display screen 102 and/or additional audio guidance is provided through the device earphone (not shown). For example, present an image (or his or her own iris image) on the display screen 102, the patient can adjust the distance between the ocular lenses 104 and the display screen 102 until the image on the display screen 102 is on focus (clear and sharp) to his or her eyes. The refractive error is then corrected and the display screen 102 is at the patient's retina conjugate.

With the device described in FIG. 3, if the on-axis cameras 303 are operated in the retina mode and there is a coupled focusing adjustment mechanism 301 between the on-axis cameras 303 and the display screen 300, the manual refractive error correction procedure described above can also place the on-axis cameras 303 at the patient's retina conjugate at the same time.

The refractive error correction can also be automated with the device described in FIG. 1 or FIG. 3, if the on-axis cameras 101 or 303 can be operated in retina mode. Similar to the auto focus function in a common camera, the contrast of the captured retina images can be used to set the cameras focus on the retina surface. If the coupled focusing adjustment mechanism 307 is employed, the display screen 300 is also automatically focused to the patient's eye when the on-axis cameras 304 are focused on the retina.

Figure 4A:
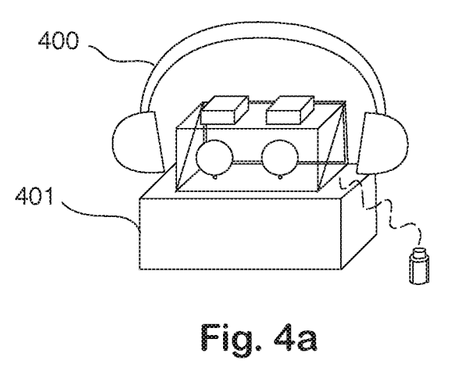
FIG. 4a is an illustration of a battery powered wearable ophthalmic device and is charged with a docking station while it is not in use.
Figure 4B:
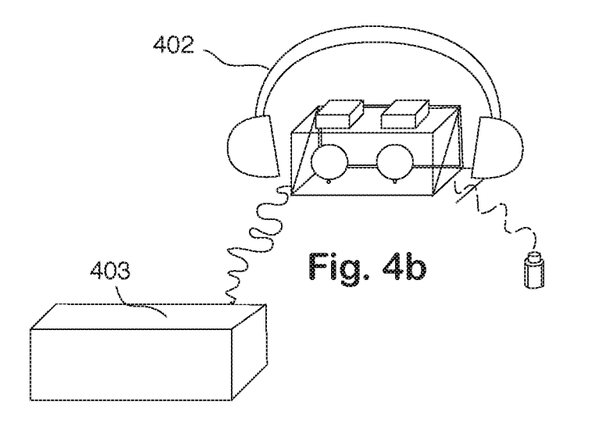
FIG. 4b is an illustration of an ophthalmic device that consists of a wearable head-mounted module and a separated chassis to host bulky and heavy optical and electrical modules.

FIG. 4a describes a battery powered wearable ophthalmic device. The head-mounted structure 400 is recharged on a docking station 401 when not in use. FIG. 4b describes a wearable ophthalmic device that uses an external DC or AC power source so that no batteries are included in the head-mounted structure 402 in order to keep the device lightweight and comfortable for the patient. The DC or AC power source is packaged in a separated chassis 403 and connected to the wearable device. For the same purpose, some bulky or heavy components can be packaged into the separated chassis 403 as appropriate.

Figure 5:
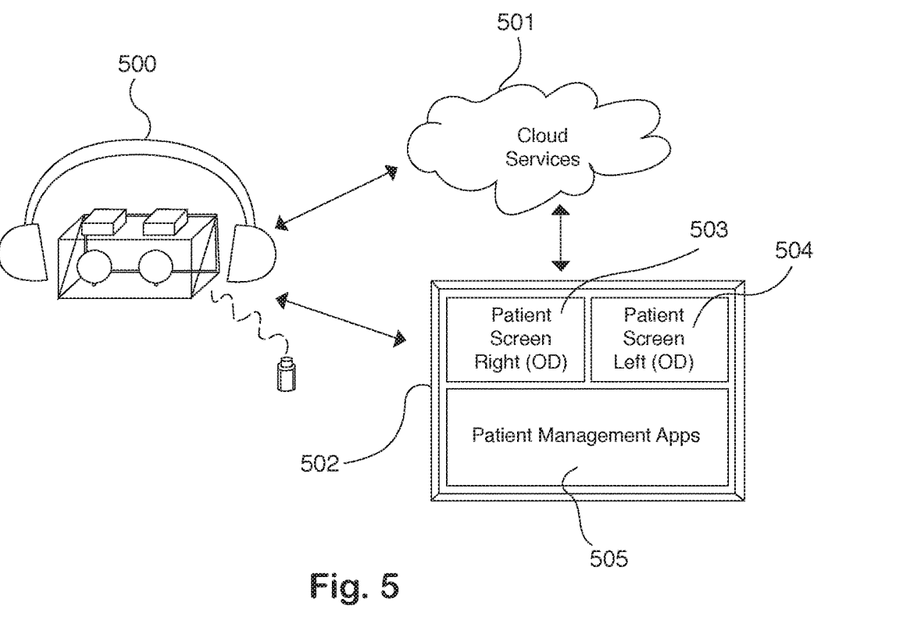
FIG. 5 is a top-level illustration of the wearable ophthalmic device and the accessory features such as the cloud based service connection ability which can be used to share test results with other permitted viewers.

FIG. 5 describes a wearable ophthalmic device 500 is wirelessly connected to a remote Cloud server 501. A software application 502 that runs on computers or mobile devices can be used to assign test protocol, access test results and monitor test progress. Additional services and advanced features can be provided through the Cloud server 501. For example, the patient's test results and reports can be stored on the server and shared with other authorized viewers anytime and anywhere. Test results are grouped in chronological order and progressive change analysis can be performed on Cloud based server. Computationally intensive algorithms can also be applied to the test data on the Cloud server 501 without increasing the complexity of the wearable device 500. A software application 502 installed and run on a computer or any mobile devices can remotely connect to the wearable ophthalmic device 500 and the Cloud server 501. Medical professionals or the patient him- or herself can use the software application 502 to assign test protocols to the patient in advance, review test results after the test is complete. During the test, another person or a medical professional can also use the software application 502 to monitor the test progress and interact with the patient through the windows 503 and 504 and other patient management applications 505.

Figure 6A:
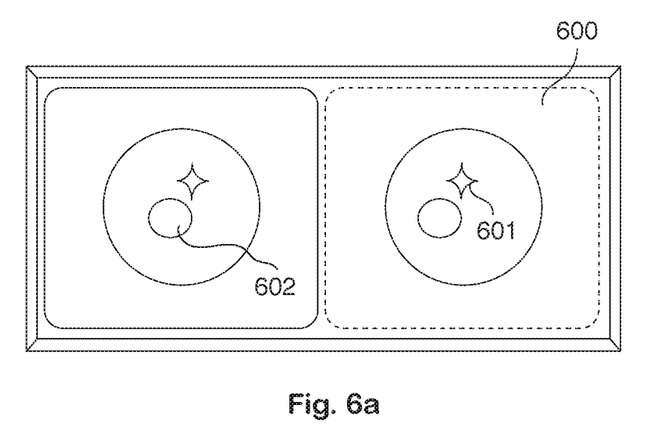
FIGS. 6a and 6b are again a front view illustration of the two individual display screens used to present the fixation targets and the stimuli for each eye based on the detected gaze direction.
Figure 6B:
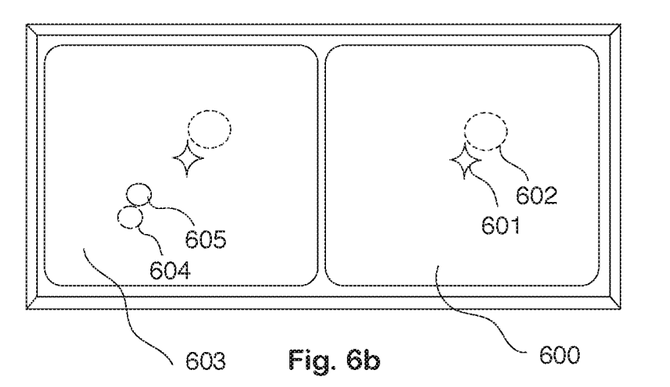

A further benefit of the present invention is to build a wearable visual field analyzer with real-time gaze detection and feedback function. FIG. 6a is a front view illustration of the two individual display screens 600 in the said wearable visual field analyzer, where the fixation targets 601 are presented for each eye. The detected gaze direction can be displayed on screen as a feedback to the patient, such as circles 602 as described in FIG. 6a. If the patient's gaze is detected off from the fixation targets 601, instructions are given to the patient to adjust his or her gaze so that the circles 602 are moved back to the fixation targets 601. FIG. 6b describes another strategy to take advantage of the real-time gaze detection and feedback function in the wearable visual field analyzer. If the patient's gaze is detected off from the fixation targets 601, the visual representation of the patient's gaze direction 602 is not displayed on the screen 600 (shown as dotted lines in the figure for explanation). Instead, the stimulus 605 to be presented at a target visual field angle 604 according to the fixation target position 601 is re-calculated and adjusted according to the patient's current gaze direction 602. This strategy ensures that the stimuli are always presented at the intended visual angles and every test is a valid test. It also essentially eliminates the need to validate the test results based on the blind spot monitoring or gaze monitoring (but no adjustment on the stimulus position 604 according to the gaze direction changes). Because the gaze feedback correction is performed in the background without the patient's notice, the test is thus more efficient and the test duration is reduced. Patient's sudden eye movements, such as blinks and saccades, etc., can also be detected with the real-time gaze detection function. Stimuli presented when these involuntary eye movements happen can be automatically re-tested to improve the test reliability.

In another embodiment, improved test results from a Fundus Camera can be achieved by using the present invention. A wearable head-mounted fundus camera 700 as described in FIG. 7a enables the user to easily capture high-quality fundus photographs all by him or herself without any medical staff or another person's assistance. Such device is more assessable and useful by a larger population and in more diverse use scenarios. The included patient interface module allows self-operation of the device and improved image quality. Two sets of the on-axis cameras 701 with focusing optics for each eye are configured in retina mode to capture the fundus photographs. Two sets of the off-axis cameras 702 for each eye are used as iris cameras. A head-mounted or goggle-like structure 704 is used to hold all components still relative to the patient's head position. Finally, a push button or touch sensor 703 is implemented for the patient to control the device and capture the fundus images by him or herself. The push button or touch sensor 703 may be connected to the device with a cable such as USB connection or wirelessly such as Bluetooth connection. FIG. 7b illustrates the wearable fundus camera 705 according to another embodiment of the invention, in which all other components are the same as described in FIG. 7a except that the on-axis cameras are able to switch between the iris mode and the retina mode, and thus the off-axis cameras are not included.

Figure 7A:
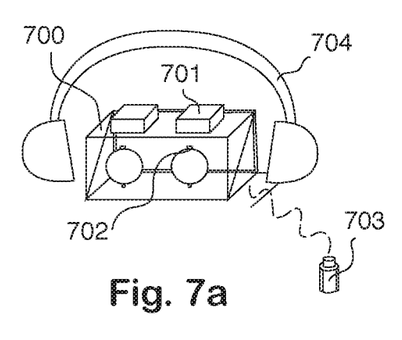
FIGS. 7a and 7b are illustrations of a wearable head-mounted fundus camera implemented with features in the present invention.
Figure 7B:
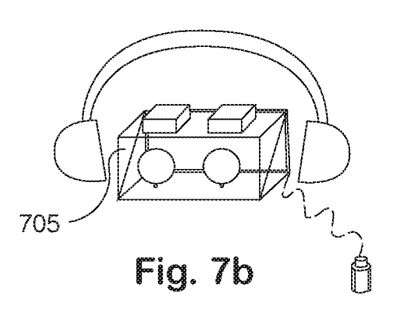

The wearable fundus camera as described in FIGS. 7a and 7b incorporate all the benefits as described above for the current invention, including (a) manual or automatic eye to device alignment supported by the iris-mode operated on-axis cameras and iris image analysis, and (b) manual or automatic refractive error correction supported by the retina-mode operated camera and a coupled focusing adjustment mechanism with the display screen.

The advantages of the wearable fundus camera are numerous. For examples, first, the patient is allowed to operate the device and trigger the capture button whenever he or she is ready, therefore any chance of involuntary eye movements (such as blinks, saccades, etc.) at the time the image is captured can be greatly diminished. Second, because the eye to device alignment remains unchanged, the patient can repeat the capture immediately at the same fixation targets to increase the success rate of obtaining a defect-free high-quality fundus image. Third, the patient can also repeat the capture as the fixation target moves to different locations so that a collection of the patient's fundus images covering a large retina area can be taken. Fourth, with the real-time gaze direction function, each fundus camera image can be associated with the actual visual field angle, not with the field angle of the presented fixation target position. It can further help stitch precisely the collection of the fundus images captured above into a larger field view. Fifth, With the design including two sets of the on-axis cameras and the illumination light sources, the fundus images can be taken for both eyes simultaneously. In fact, for cost sensitive applications, the wearable fundus camera can also be implemented with only one set of the imaging components so that the fundus image is captured for one eye at a time. The head-mounted structure is designed so that the imaging components can be flipped or translated to be able to align with the other eye.

Figure 8:
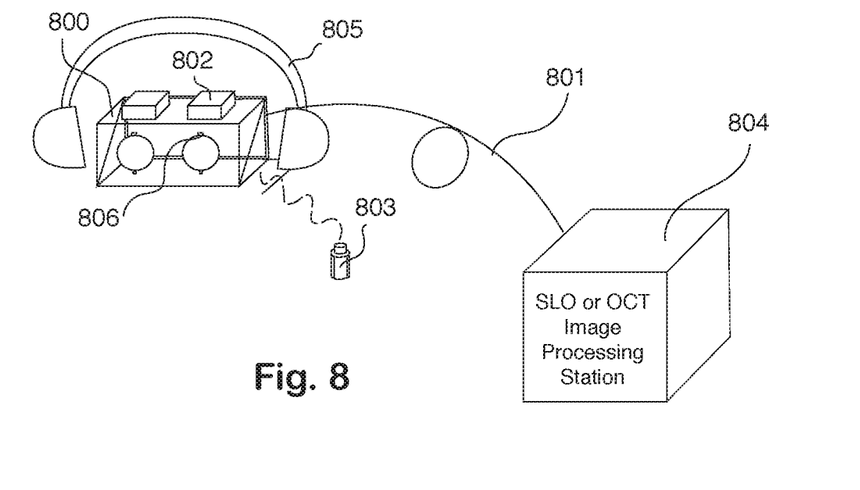
FIG. 8 is an illustration of a wearable head-mounted SLO and OCT imager that is implemented with features in the present invention.

FIG. 8 illustrates a wearable head-mounted SLO and OCT imager that is implemented with features in the present invention. The wearable (head-mounted) SLO and OCT imager 800 enables the user to easily capture high-quality SLO and OCT images all by him or herself without any medical staff or another person's assistance. The patient interface module allows self-operation of the device and improved image quality. Due to the complexity of the imaging system, it is preferable to keep most functional components and modules in a separated chassis. The improved test results from an SLO and OCT imager can be achieved by this implementation. The SLO and OCT imager provides simultaneous confocal SLO and OCT. Due to the point or line scanning nature of the SLO and OCT technologies, the on-axis cameras are replaced with laser (or light source) delivery module 802, which consists of scanning and focusing optics that direct the light beam to the target area on the patient's retina or cornea. The automated refractive error correction can be achieved by maximizing the detected light intensity as the focusing optics for the laser delivery module 802 is swept over a small range from the nominal position. There can be only one set of the laser delivery module 802 for the purpose of simplicity or cost-saving. The optical components in the laser delivery module 802 can be arranged so that the laser beam is delivered to one of the eyes and then switched to the other eye as needed. The implementation of the optical signal detection module for the SLO and the OCT imagers can vary widely depending on the technologies and techniques involved. In the present invention, in order to keep the head-mounted module lightweight, it is preferable to keep most functional components and modules in a separated chassis 804, which may include the light source, the signal detection module, computer, control unit and power supply, etc. The chassis 804 and the head-mounted module 800 are connected through electrical and optical cables 801. It is important that a patient interface module 803 is included so that the patient can trigger the image acquisition when he or she is ready. The off-axis cameras 806 are also included to support eye to device alignment, blinks and/or saccades detection and monitor the gaze direction during the image scans. Due to the scanning nature of the SLO and OCT imaging technology, it is usually take seconds to complete the image acquisition. Motion artifacts are almost inevitable in the acquired images due to the head and/or eye movements in traditional SLO and OCT imagers.

With the wearable SLO and OCT imagers described in present invention, however, the head to device alignment remains unchanged throughout the test, and the device has essentially unlimited time window to keep scanning and acquiring data points. Data points acquired during an eye movement, such as a blink or a saccade, are detected and rejected until every data point within the targeted scan area are validated as motion-free.

Another advantage with the present invention is that the data acquisition can be paused and resumed because the same eye to device alignment can be restored and maintained.

A fast iris and pupil detection algorithm can also be implemented to track the patient's gaze and the gaze direction can then be fed back to the optical scan controller in real time. If the patient's gaze is shifted away from the fixation target, the optical scanner applies with appropriate offsets accordingly to make sure the laser beam is projected to the correct locations on the retina. With recorded gaze data, post-acquisition analysis can also be implemented to reveal the physical locations of the laser beam on the patient's retina, which is then used to register each frame or pixel in the image. This is very useful to remove motion artifacts that are common in SLO and OCT images.

Although one or more embodiments of the ophthalmic device have been described in detail, one of ordinary skill in the art will appreciate the modifications to the component selection, and design of the individual high definition screens with on-axis "iris" cameras, beam splitter, etc. orientation. It is acknowledged that obvious modifications will ensue to a person skilled in the art. The claims which follow will set out the full scope of the invention.

The invention claimed is:

1. A wearable ophthalmic device for a patient to conduct a self-operable eye test comprising: a head-mounted structure and an interface module,
   the head-mounted structure comprising a plurality of ocular lens,
   at least one infrared illumination LED, and
   at least one display screen to present a visual field test stimuli fixed to an inner side of the head-mounted structure;
   wherein the interface module is hand-held and comprises at least one push button operably coupled to the head-mounted structure wirelessly or via a cable.

2. The wearable ophthalmic device of claim 1, further comprising at least one on-axis camera.

3. The wearable ophthalmic device of claim 2, further comprising at least one beam splitter.

4. The wearable ophthalmic device of claim 1, further comprising at least one off-axis camera.

5. The wearable ophthalmic device of claim 1, wherein the at least one display screen comprises two divide portions, one dedicated for the patient's right eye and the other dedicated for the patient's left eye.

6. The wearable ophthalmic device of claim 1, wherein the interface module is an assembly of one or more sensor that collect the patient's various responses.

7. The wearable ophthalmic device of claim 1, wherein the visual field test stimuli are presented on the at least one display screen and the patient responses are collected from the interface module, allowing the patient's non-testing eye to remain open and optionally fixated to a fixation target.

8. The wearable ophthalmic device of claim 1, wherein the device wirelessly connects and transmits results to a Cloud server to be reviewed remotely.

9. A wearable ophthalmic device for a patient to conduct a self-operable eye test comprising: a head-mounted structure and an interface module,
   the head-mounted structure comprising a plurality of ocular lens,
   at least one infrared illumination LED, and
   at least one on-axis camera;
   wherein the interface module is hand-held and comprises at least one push button operably coupled to the head-mounted structure wirelessly or via a cable.

10. The wearable ophthalmic device of claim 9, wherein the at least one on-axis camera is used for taking iris images.

11. The wearable ophthalmic device of claim 9, wherein the at least one on-axis camera is used for taking fundus images.

12. The wearable ophthalmic device of claim 11, further comprising at least one off-axis camera for taking an iris image.

13. The wearable ophthalmic device of claim 11, wherein the at least one on-axis camera is mechanically coupled to the at least one display screen, so the at least one on-axis camera is focused on a fundus when the patient's eye is focused on the at least one display screen.

14. The wearable ophthalmic device of claim 9, further comprising at least one display screen to present fixation targets fixed to an inner side of the head-mounted structure.

15. The wearable ophthalmic device of claim 14, further comprising a beam splitter to combine two optical paths of the at least one display screen and the at least one on-axis camera.

16. The wearable ophthalmic device of claim 9, wherein the device wirelessly connects and transmits results to a Cloud server to be reviewed remotely.

17. A wearable ophthalmic device for a patient to conduct a self-operable eye test comprising:
   a head-mounted structure, an imaging processing device connected to the head-mounted structure via at least one optical cable and at least one electrical cable, and an interface module;
   the head-mounted structure comprising:
   a laser delivery module,
   at least one off-axis camera for taking an iris image,
   at least one infrared illumination LED,
   a beam splitter,
   at least one display screen to present fixation targets fixed to an inner side of the head-mounted structure;

wherein the interface module is hand-held and comprises at least one push button operably coupled to the head-mounted structure wirelessly or via a cable.

18. The wearable ophthalmic device of claim 17, wherein the imaging processing device comprises either a confocal scanning laser ophthalmoscopy (SLO) or an optical coherence tomography (OCT).

19. The wearable ophthalmic device of claim 17, wherein the device wirelessly connects and transmits results to a Cloud server to be reviewed remotely.

* * * * *